United States Patent [19]

Allen

[11] 4,427,780

[45] Jan. 24, 1984

[54] METHOD FOR ASSAYING VITAMIN-CONTAINING COMPOSITIONS FOR VITAMIN ANALOGUES

[75] Inventor: Robert H. Allen, Englewood, Colo.

[73] Assignee: University Patents, Inc., Norwalk, Conn.

[21] Appl. No.: 292,370

[22] Filed: Aug. 13, 1981

[51] Int. Cl.$^3$ .................. G01N 33/58; G01N 33/60
[52] U.S. Cl. .................. 436/505; 436/542; 436/177; 436/804; 436/822
[58] Field of Search .......... 424/1; 436/505, 804, 436/542, 177, 822

[56] References Cited

U.S. PATENT DOCUMENTS

| | | | |
|---|---|---|---|
| 4,188,189 | 2/1980 | Allen | 424/1 |
| 4,332,786 | 6/1982 | Cabelli et al. | 424/1 |
| 4,333,918 | 6/1982 | Carney et al. | 424/1 |

OTHER PUBLICATIONS

Kolhouse et al., N. Eng. J. Med., 299(15), 785–792 (1978).
LeFebvre et al., Chemical Abstracts, 93(21), 1980, #200436d.
Rothenberg, Chemical Abstracts, 94(17), 1981, #131819n.
Kolhouse et al., J. Clin. Invest., 60(6), 1381–1392 (1977).
Kolhouse et al., Chemical Abstracts, 88(13), 1978, #85428k.

*Primary Examiner*—Christine M. Nucker
*Attorney, Agent, or Firm*—George M. Yahwak

[57] ABSTRACT

Vitamin-containing multicomponent compositions are assayed to determine the extent of conversion of the vitamin to one or more analogues thereof due to interaction between the vitamin and the other components of the composition, employing a radioactive labeled form of the vitamin. The assay is useful for quality control in the manufacture of multivitamin and multivitamin-mineral formulations and vitamin-supplemented foods intended for human or animal ingestion.

7 Claims, No Drawings

METHOD FOR ASSAYING VITAMIN-CONTAINING COMPOSITIONS FOR VITAMIN ANALOGUES

The invention described herein was made in part in the course of work under a grant or award from the Department of Health, Education and Welfare.

BACKGROUND OF THE INVENTION

This invention relates to a vitamin assay, and, more particularly, to an assay for determining the extent of conversion of a vitamin to one or more analogues thereof due to interaction between the vitamin and the other components of a multicomponent composition containing the vitamin.

Multivitamins are frequently ingested in the form of pills, and are frequently used to supplement human foods and a variety of animal chows. Vitamins are chemicals and are capable of reacting among themselves and with other substances to form vitamin analogues. Despite this knowledge, little, if any, attention has been paid to the possibility that vitamin analogues might be formed in multivitamin pills, supplemented foods, and animal chows. Essentially no attention has been paid to the possibility that vitamin analogues might be harmful in the sense that they might be absorbed from the gastrointestinal tract and might interfere with the activities of various enzymes that require vitamins for activity.

This lack of awareness and concern is readily apparent from the standard production procedures and quality control methods that are employed in the pharmaceutical industry, and the human and animal food industries. These procedures consist of adding known amounts of various vitamins to a given preparation, and then assaying the amounts of the individual vitamins present after the preparation has been manufactured and stored under normal conditions. "Losses" are frequently encountered, and this problem is remedied by simply increasing the amounts of individual vitamins that are added to the preparations. The reason for the "loss" is not explored, and no attention is given to the possibility that such "losses" might actually represent the conversion of vitamins into vitamin analogues, rather than the complete destruction or evaporation of the vitamins themselves. The problem of identifying vitamin analogues, at least by means of standard analytical techniques, is an extremely difficult one, because so many different vitamins are present in multivitamin and multivitamin-mineral formulations, supplemented foods and animal chows.

Recent studies conducted by the present inventor have shown that CN-cobalamin is converted to a number of cobalamin analogues by the concerted action of vitamin C, thiamine, and copper sulfate. These studies have also shown that such interactions are responsible for the presence of cobalamin analogues in a number of popular multivitamin-mineral pills and animal chows, and that additional cobalamin analogues are formed when these preparations are merely dissolved in water and incubated at body temperature for several hours. In addition, these studies have shown that such cobalamin analogues are absorbed from the gastrointestinal tract of laboratory animals, and that they either lack cobalamin activity or actually inhibit cobalamindependent enzymes, when they are injected parenterally into laboratory animals. These findings suggest that cobalamin analogues are being ingested by humans, and that they may be detrimental. It is furthermore suggested by these studies that other vitamins may be converted into analogues in various multivitamin preparations, and that these analogues may also be detrimental.

SUMMARY OF THE INVENTION

It is, accordingly, a primary object of the present invention to provide a novel assay technique for determining the extent of conversion of a vitamin to one or more analogues thereof due to interaction between the vitamin and the other components of a multicomponent composition containing the vitamin.

Another object of the invention is to provide an assay technique in accordance with the preceding object, which may be readily adapted for quality control in the manufacture of various multivitamin and multivitamin-mineral formulations and vitamin-supplemented foods intended for human or animal ingestion.

A further object of the invention is to provide an assay technique in accordance with the preceding objects, which is relatively simple and economical to carry out.

Still another object of the invention is to provide an assay technique in accordance with the preceding objects, which is particularly suitable for use in detecting the conversion of cobalamin (vitamin $B_{12}$) to analogues thereof in cobalamin-containing formulations.

The above and other objects are achieved in accordance with the present invention, by means of an assay procedure based on radioactive detection techniques, and employing as its principal reagent a radioactive labeled form of the vitamin whose extent of conversion to analogues is to be measured. The assay is carried out by first forming an aqueous incubation mixture comprising a sample of the composition to be assayed and containing a known quantity of the radioactive labeled vitamin reagent. The incubation mixture is then incubated for a period of time sufficient to enable any conversion of tha radioactive labeled vitamin to analogues thereof to occur by interaction of any sample components reactive therewith. Following the incubation step, the incubation mixture is fractionated to obtain a fraction rich in the vitamin in question and substantially devoid of analogues thereof and which, in the absence of any conversion in the incubation step, would have contained a known percentage of the known quantity of the radioactive labeled vitamin reagent. The content of the radioactive labeled vitamin in such fraction is then measured by standard radioactive detection techniques. The extent of conversion of the vitamin to one or more analogues thereof due to interaction between the vitamin and the other components of the composition being assayed, can then be readily determined as the percent difference between (i) the expected content of the radioactive labeled vitamin in the fraction based upon such known percentage, and (ii) the measured content of the radioactive labeled vitamin in the fraction.

DESCRIPTION OF PREFERRED EMBODIMENTS

The assay procedure of the present invention may suitably be employed for determining the extent of conversion of any given vitamin to one or more analogues thereof due to interaction between such vitamin and the other components of a multicomponent composition containing such vitamin. The procedure is particularly well suited as a quality control technique in the manufacture of various commercial multivitamin and multivitamin-mineral formulations, vitamin-supplemented foods, and animal chows.

The radioactive labeled vitamin reagent for use in the assay of the present invention, may be readily prepared by standard radioactive labeling techniques well known in the art, or obtained from any of a number of commercial sources. Suitable radioactive labels include, for example, $^{57}$Co, $^{58}$Co, and the like.

In carrying out the assay of the present invention, an aqueous incubation mixture is first formed comprising a sample of the composition to be assayed and containing a known quantity of the radioactive labeled vitamin reagent. Ideally, the sample is formulated so as to contain the radioactive labeled vitamin reagent in place of and in the same proportion as the unlabeled form of the vitamin normally present in the composition to be assayed. However, substantially identical results will be obtained if the sample employed in the assay contains the unlabeled form of the vitamin in the proportion normally present in the composition, and the radioactive labeled vitamin reagent is incorporated into the incubation mixture in a trace known amount in addition to the unlabeled vitamin.

The incubation mixture is suitably formed by homogenizing the composition sample in an aqueous medium, for example, by blending the sample with the aqueous medium in a Waring Blender at 4° C. for 5 one-minute intervals, with cooling in an ice water bath between the homogenization intervals to insure that the temperature does not exceed 8° C. at any time during the homogenization procedure. Removal of any solid residue may be effected by centrifugation. When not present as an integral part of the sample formulation, the radioactive labeled vitamin reagent is then added to the homogenized sample in a trace known amount, e.g., in an amount within the range of from about 0.1 to about 5.0 pmol.

The incubation mixture is then incubated for a period of time sufficient to enable any conversion of the radioactive labeled vitamin reagent to analogues thereof to occur by interaction of any sample components reactive therewith. Such incubation will typically be carried out at physiologic temperatures, i.e., at about 37° C., for a time period of at least about two hours.

Following the incubation step, the incubation mxiture is then fractionated to obtain a fraction rich in the vitamin of interest and substantially devoid of analogues thereof. Such fractionation may suitably be carried out by first isolating substantially all of the content of the vitamin in question from the incubation mixture, for example, by reverse affinity chromatography; and thereafter separating the isolated vitamin content into a plurality of fractions, for example, by paper chromatography, from which a peak fraction is selected for the subsequent measuring step. Such peak fraction, as well as the percentage of the starting quantity of the radioactive labeled vitamin reagent which should be present therein in the absence of any conversion of the radioactive labeled vitamin reagent to analogues thereof during the incubation step, will generally be known from prior experience. Alternatively, they may be readily determined during the course of the assay procedure by adding to the isolated vitamin content prior to its being separated into a plurality of fractions a trace known amount of a second radioactive labeled form of the vitamin in question which is readily distinguishable from the radioactive labeled vitamin reagent. By way of example, if the reagent is radioactive labeled with $^{57}$Co, the distinguishable second radioactive labeled form of the vitamin may be labeled with $^{58}$Co. Separate measurement of the content of the second radioactive labeled vitamin in each of the fractions by standard radioactive detection techniques well known in the art, will locate the peak fraction and provide the percentage of the starting quantity of the radioactive labeled vitamin reagent which should be present in such peak fraction in the absence of any conversion thereof to analogues.

Following the fractionation step, the content of the radioactive labeled vitamin reagent present in the peak fraction is measured by standard radioactive detection techniques well known in the part. The percent difference is then calculated between (i) the expected content of the radioactive labeled vitamin reagent in the fraction, based upon the known percentage of the starting quantity of the radioactive labeled vitamin reagent which should be present in the fraction in the absence of any conversion thereof to analogues, and (ii) the actual measured content of the radioactive labeled vitamin reagent in the fraction. Such percent difference represents the extent of conversion of the vitamin of interest to one or more analogues thereof due to interaction between such vitamin and the other components of the composition being assayed.

The invention is further illustrated by way of the following example.

EXAMPLE 1

Several different commercially obtained cobalamin-containing multivitamin pills and multivitamin-mineral pills were each assayed by the following procedure to determine the extent of conversion of their cobalamin content to cobalamin analogues due to interaction between the cobalamin and the other pill components.

The pills were homogenized in water, 10 ml per pill, at 4° C. for 5 one-minute intervals in a Waring Blender. The samples were cooled in an ice water bath between the homogenization intervals to insure that the temperature did not exceed 8° C. at any time during the homogenization procedure. Following homogenization, the samples were stirred at 4° C. for one hour and centrifuged at 20,000×g for 30 minutes. A trace known amount of CN-[$^{57}$Co]cobalamin (0.1 to 5.0 pmol) was added to supernatant and the samples were incubated at 37° C. for 2 hours. The samples were then cooled to 4° C. in an ice water bath, and the cobalamin was purified by reverse affinity chromotography on hog R protein-Sepharose, followed by phenol extraction. A trace amount of CN-[$^{58}$Co]cobalamin (10 pmol) was added to the purified samples, which were then fractionated by paper chromatography on Whatman 3 MM paper in a solvent consisting of 880 ml of sec-butanol, 8.2 ml of glacial acetic acid, 6.2$\mu$ mol of HCN and a saturating amount (approximately 425 ml) of water. Paper chromatograms were dried in a fume hood at 22° C. for one hour, cut into 38 equal fractions, and assayed for $^{57}$Co and $^{58}$Co using a refrigerated Beckman Gamma 8000 System (Beckman Instruments, Inc., Fullerton, California). The percent of Co present as [$^{57}$Co]cobalamin analogues was calculated by dividing the percent $^{58}$Co in the peak fraction (expressed as percent of the $^{58}$Co present in the entire 38 fractions) into the percent $^{57}$Co present in the same fraction (expressed as percent of the $^{57}$Co present in the entire 38 fractions), subtracting this value from 1.00, and multiplying by 100.

The results of the assays indicated that none of the CN-[$^{57}$Co]cobalamin was converted to [$^{57}$Co]cobalamin analogues with any of the multivitamin pills not containing minerals. The conversion of CN-[$^{57}$Co]cobalamin to [$^{57}$Co]cobalamin analogues was, however, observed with each of the multivitamin-mineral pills which were assayed. The extent of such conversion varied with the formulation from as low as 16% to as high as 90%.

I claim:

1. A method for assaying a vitamin-containing multicomponent composition to determine the extent of conversion of said vitamin to one or more analogues thereof comprising the steps of:
   (a) adding a known quantity of a radioactive labeled form of said vitamin to be assayed to a sample of said composition;
   (b) incubating the mixture obtained in step (a) for a sufficient period of time to enable conversion of said radioactive labeled vitamin to vitamin analogues by the interaction of components of said mixture;
   (c) fractionating said incubated mixture of step (b) into a vitamin rich fraction and a vitamin poor fraction, said vitamin rich fraction being rich in said vitamin to be assayed and substantially devoid of vitamin analogues formed in step (b); and
   (d) measuring the content of radioactive labeled vitamin in said vitamin rich fraction.

2. The method of claim 1, wherein the sample contains said vitamin to be assayed in the proportion normally present in said composition, and said radioactive is added in a trace amount.

3. The method of claim 1, further comprising homogenizing said sample to incubating the mixture.

4. The method of claim 1, wherein said incubating is at physiologic temperatures for a time period of at least about 2 hours.

5. The method of claim 1, wherein said composition is selected from the group consisting of multivitamin formulations, multivitamin-mineral formulations, and vitamin-supplemented foods.

6. The method of claim 1, wherein said vitamin is cobalamin.

7. A method for assaying a vitamin-containing multicomponent composition to determine the extent of conversion of said vitamin to one or more analogues thereof comprising the steps of:
   (a) adding a known quantity of a radioactive labeled form of said vitamin to be assayed to a sample of said composition;
   (b) incubating the mixture obtained in step (a) for sufficient period of time to enable conversion of said radioactive labeled vitamin to vitamin analogues by the interaction of components of said mixture;
   (c) fractionating said incubated mixture of step (b) into a vitamin rich fraction and a vitamin poor fraction, said vitamin rich fraction being rich in said vitamin to be assayed and substantially devoid of vitamin analogues formed in step (b); and
   (d) measuring the content of radioactive labeled vitamin in said vitamin poor fraction.

* * * * *